(12) United States Patent
Shinoda et al.

(10) Patent No.: US 6,372,880 B1
(45) Date of Patent: Apr. 16, 2002

(54) COPOLYMER AND PROCESS FOR PREPARING THE SAME

(75) Inventors: Hosei Shinoda; Yukiko Asou; Hiroaki Tamatani, all of Kanagawa (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/219,452

(22) Filed: Dec. 23, 1998

(30) Foreign Application Priority Data

Dec. 25, 1997 (JP) .............................................. 9-358356

(51) Int. Cl.⁷ .................. C08G 63/44; C08G 69/00; C08G 73/10; A61K 31/74; A61K 9/48; A61K 9/52

(52) U.S. Cl. .................... 528/310; 424/78.08; 424/451; 424/457; 528/322; 528/328; 528/363

(58) Field of Search .................... 424/451, 456, 424/70.1, 70.2, 70.4, 70.6, 70.9, 70.11, 70.122, 70.13, 70.17, 78.03, 400, 401, 457, 78.08; 548/485–6, 546–7; 528/328, 363

(56) References Cited

U.S. PATENT DOCUMENTS

| | | |
|---|---|---|
| 4,767,628 A | 8/1988 | Hutchinson |
| 5,175,285 A * | 12/1992 | Lehmann et al. ........... 544/141 |
| 5,686,066 A * | 11/1997 | Harada et al. ............ 424/70.14 |

FOREIGN PATENT DOCUMENTS

| | | |
|---|---|---|
| EP | 0531091 | 3/1993 |
| JP | 02209918 | 8/1990 |
| WO | WO/94/01486 | 1/1994 |

OTHER PUBLICATIONS

Jain et al, "Syntheses and Characterization of Random Copolymers of Aspartic Acid with Lactic Acid and Glycolic Acid", Makromol. Chem. vol. 182, pp. 2557–2561, 1981.

* cited by examiner

*Primary Examiner*—Shelley A. Dodson
(74) *Attorney, Agent, or Firm*—Burns, Doane, Swecker & Mathis, L.L.P.

(57) ABSTRACT

A copolymer having a weight-average molecular weight of 1,000 to 100,000 which comprises, as repeating structure units, both of a succinimide unit represented by the structural formula (1)

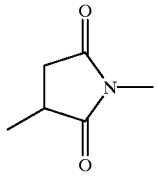

(1)

and a hydroxycarboxylic acid unit represented by the structural formula (2)

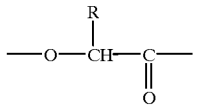

(2)

wherein R is a methyl group or a hydrogen atom, and a process for preparing a copolymer which comprises a polymerization step of heating a mixture of aspartic acid and a cyclic ester compound.

14 Claims, No Drawings

COPOLYMER AND PROCESS FOR PREPARING THE SAME

BACKGROUND OF THE INVENTION

1. Field of the Invention

The present invention relates to a copolymer which is a novel compound useful as a base material for a sustained releasing drug and which has both of a succinimide unit and/or an aspartic acid unit as well as a lactic acid unit and/or a glycolic acid unit, and a process for preparing the above copolymer.

2. Description of the Related Art

Heretofore, there has been the approach of applying a biologically absorbable polymer to a DDS (a drug delivery system). The DDS means a system in which a drug including the biologically absorbable polymer as a base material can be sustaining-released by a proper technique.

Here, typical examples of the above proper technique include a method of blending the biologically absorbable polymer with the drug, a method of microcapsulating the drug with the biologically absorbable polymer, and a method of immobilizing the drug on the biologically absorbable polymer.

Typical examples of the above biologically absorbable polymer include poly-α-hydroxy acids such as a polylactic acid (PLA) and a polyglycolic acid (PGA).

For example, Japanese Patent Application Laid-Open No. 64824/1987 discloses a method which comprises subjecting, to a ring opening polymerization, glycolide (GLD) which is a cyclic dimer of glycolic acid and lactide (LTD) which is a cyclic dimer of lactic acid, thereby obtaining a low-molecular weight polydisperse lactic acid-glycolic acid copolymer (PLGA) useful as the base material for a sustained releasing drug.

On the other hand, in the DDS just described, the sustained releasing behavior of the drug in which the biologically absorbable polymer is used as the base material of the sustained releasing drug is known to variously change on the basis of a specific interaction between the drug and the biologically absorbable polymer. In recent years, therefore, it has been desired to make the drugs having various structures sustained releasable, but only by selecting the biologically absorbable polymer as the base material from already existent polymers such as PLGA, it is often difficult to design the DDS which can express a desired sustained release speed, sustained release period, sustained release pH and the like.

In view of such a technical background, a novel biologically absorbable polymer material has been desired as the base material for the sustained releasing drug.

Furthermore, when the sustained releasing drug having a form of microspheres, microcapsules or the like is manufactured by an emulsion method which has heretofore been used, an organic solvent is used and hence a solvent removal step is required, so that it is necessary to validate that the remaining solvent in the drug is at such a level as to be substantially acceptable.

Accordingly, there is also a demand that a drug formulation can be achieved without using any solvent by thermally melting the polymer and then mixing it with the drug. However, for example, an optically active PLA has a melting point of 160 to 180° C., and if it is molten at this temperature, there exists a problem that the drug thermally decomposes. If the molecular weight of the PLA is reduced, the melting point also lowers, but according to the knowledge of the present inventors, the PLA has a high melting point of 120° C. or more even at a molecular weight of about 2000 to 3000. On the other hand, if the molecular weight of the PLA is less than the above level, the PLA becomes a syrup state, which makes it difficult to prepare the microspheres or the like. Therefore, it has been desired that the biologically absorbable polymer which can be used particularly as the base material for the sustained releasing drug among medical materials has a low melting point.

Ganpat L. Jain et al. disclose a certain kind of random copolymer of lactic acid and aspartic acid [Ganpat L. Jain et al., Makromol. Chem., Vol. 182, p. 2557–2561 (1981)]. Herein, Jain et al. describe a technique in which aspartic acid and lactic acid are subjected to dehydration-polycondensation at an aspartic acid/lactic acid ratio of 2:1 to 0.5:1 at 150° C. under reduced pressure for 5 hours to obtain a lactic acid-aspartic acid copolymer of aspartic acid:lactic acid=9:1 to 1.77:1.

However, when lactic acid is copolymerized with aspartic acid by this technique, a low-molecular weight random copolymer having a wide molecular weight distribution is merely obtained, and its yield is also low. In addition, this polymer has a high melting point, and it is poor in melting workability and moldability and its use as a medical material is restricted.

SUMMARY OF THE INVENTION

An object of the present invention is to provide a novel copolymer and process for preparing the same, which is suitable as, for example, a base material for a sustained releasing drug, can typically be softened or molten in such a low temperature range that a drug for use in a DDS does not thermally decompose, is an unsticky solid at ordinary temperature (e.g., 25° C., or less than 40° C.), and is soluble in various kinds of solvents.

The present inventors have intensively investigated with the intention of achieving the above objects, and as a result, it has been found that when aspartic acid is heated together with lactide, glycolide or the like to perform polymerization, a novel biologically absorbable copolymer having both of a hydroxycarboxylic acid unit and a succinimide unit in its structure can be obtained, and this copolymer is solid at ordinary temperature, is molten at 100° C. or less, is soluble in various kinds of solvents, and shows a particular hydrolysis behavior. In consequence, the present invention has been completed.

That is to say, the present invention is directed to a copolymer having a weight-average molecular weight of 1,000 to 100,000 which comprises, as repeating structure units, both of a succinimide unit represented by the structural formula (1)

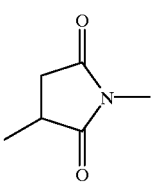

(1)

and a hydroxycarboxylic acid unit represented by the structural formula (2)

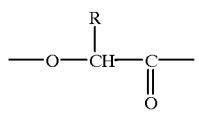

(2)

wherein R is a methyl group or a hydrogen atom.

Furthermore, the present invention is directed to a process for preparing a copolymer which comprises a polymerization step of heating a mixture of aspartic acid and a cyclic ester compound to obtain the copolymer having both of a succinimide unit and a hydroxycarboxylic acid unit as repeating structural units.

DETAILED DESCRIPTION OF THE PREFERRED EMBODIMENTS

The structure of a copolymer according to the present invention which has at least both of a succinimide unit and a hydroxycarboxylic acid unit as repeating structure units can be confirmed by a known analytical means such as a nuclear magnetic resonance (NMR) spectrum measurement or an infrared absorption (IR) spectrum measurement.

For example, according to the IR spectrum measurement, there can be observed characteristic absorptions of a carbonyl bond of the succinimide unit as well as another carbonyl bond of a lactic acid unit and/or a glycolic acid unit.

Furthermore, for example, according to the NMR spectrum measurement, there can be clearly confirmed peaks derived from a methylene proton and a methine proton of the succinimide unit as well as peaks derived from a methyl proton and a methine proton of the lactic acid unit and/or a methylene proton of the glycolic acid unit. When an NMR measuring device having a high resolving power is used, there can be slightly observed fine peaks such as peaks derived from a proton of an amide group and a methyl proton adjacent to the amide group as well as peaks derived from branches and chain sequences (inclusive of groups adjacent to the succinimide unit, the aspartic acid unit, the lactic acid unit and/or the glycolic acid unit).

A typical example of the copolymer according to the present invention is a copolymer having a highly dimensional structure which is called a block polymer, a graft polymer, a graft block polymer or a hyper branched polymer in this polymeric chemical field. More concretely, the example of the copolymer is a copolymer having a structure in which a polysuccinimide segment mainly having the succinimide unit as the repeating structure unit is linked with a polyhydroxycarboxylic acid segment having the hydroxycarboxylic acid unit as the repeating structure unit in a block state and/or a branched state.

The block polymer, graft polymer, graft block polymer or hyper branched polymer of the present invention preferably comprises both of a polysuccinimide segment represented by the structural formula (3)

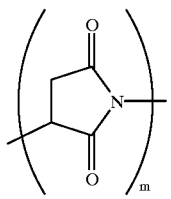

(3)

wherein m is an integer of 1 to 100, and a polyhydroxycarboxylic acid segment represented by the structural formula (4)

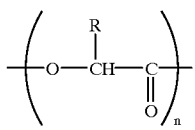

(4)

wherein R is a methyl group or a hydrogen atom; and n is an integer of 1 to 1,000, and in which the ratio of the succinimide unit is in the range of 1 to 33 mol %, and the ratio of the hydroxycarboxylic acid unit is in the range of 67 to 99 mol %.

Furthermore, one example of the copolymer of the present invention is a polymer having a structure represented by the following structural formula (12):

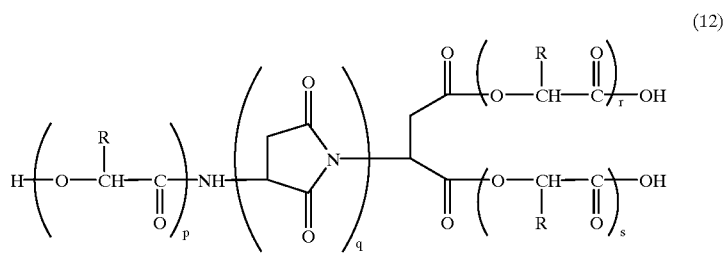

(12)

wherein p, r and s are each 0 or a positive integer, provided that three of p, r and s are not simultaneously 0; q is an integer of 1 or more, and $(p+r+s)/(q+1)$ is in the range of 2 to 100; and R is a hydrogen atom or a methyl group.

In this case, fundamentally, each of a polysuccinimide chain and a polyhydroxycarboxylic acid chain has a blocking tendency, and these chains are each present as a segment in the molecule of the copolymer.

Furthermore, in the copolymer of the present invention, at least a part of the succinimide unit can be in the ring opening state. In this case, the copolymer is preferably a branched copolymer having all of a segment A represented by the structural formula (5)

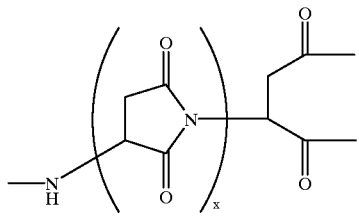
(5)

wherein x is an integer of 1 to 100, a segment B represented by the structural formula (6)

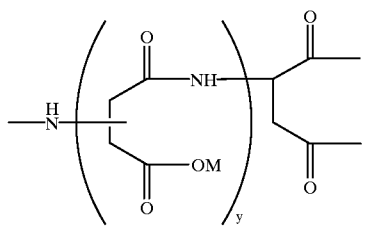
(6)

wherein y is 0 or a positive integer of 100 or less; and M is a metal or a hydrogen atom, and a segment C represented by the structural formula (7)

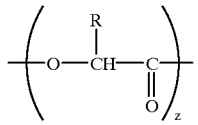
(7)

wherein z is an integer of 4 to 1,000; and R is a methyl group or a hydrogen atom.

Furthermore, the copolymer of the present invention can include aspartic acid units represented by the following structural formulae (9) and (10) jumbled in the polysuccinimide segment.

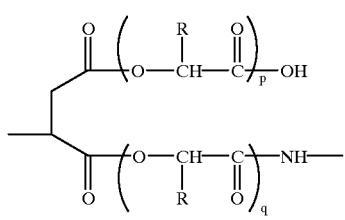
(9)

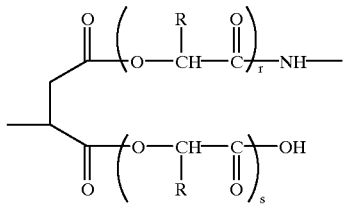
(10)

wherein p, q, r and s are each 0 or a positive integer of 1000 or less; and R is a methyl group or a hydrogen atom.

Moreover, the carboxyl group at the terminal of the molecular chain is not always a COOH group. For example, it may form a salt with a base such as an alkali metal, an alkaline earth metal or an amine.

In view of physical properties and the like, the molecular weight of the copolymer according to the present invention is in the range of 1,000 to 100,000 in terms of its weight-average molecular weight.

With regard to the composition of the copolymer according to the present invention, it is preferred that the ratio of the succinimide unit is in the range of 1 to 33 mol %, and the ratio of the hydroxycarboxylic acid unit is in the range of 67 to 99 mol %. In the case that at least a part of the succinimide unit is in the ring opening state, it is preferred that the ratio of the unit including the structure represented by the following structural formula (11) which is derived from aspartic acid is in the range of 1 to 33 mol %:

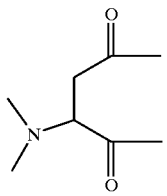
(11)

and the ratio of the hydroxycarboxylic acid unit is in the range of 67 to 99 mol %. The unit including the structure represented by the above structural formula (11) which is derived from aspartic acid is a general term for the succinimide unit and a polyaspartic acid unit obtained by the ring opening of this succinimide unit.

Next, a process for preparing the copolymer of the present invention will be described.

One process for preparing the copolymer of the present invention is characterized by heating a mixture of aspartic acid and a cyclic ester compound.

Aspartic acid which can be used herein may be an optically active L-form, D-form or DL-form. In order to obtain the copolymer having a high-molecular weight, it is preferable to use high-purity aspartic acid in which the content of impurities such as fumaric acid and maleic acid is 1% by weight or less.

The cyclic ester compound which can be used herein is a compound in which a hydroxycarboxylic acid is dehydrated and cyclized, and preferable examples of the cyclic ester compound include lactide, glycolide, caprolactone, propiolactone, butyrolactone and valerolactone, and lactide and glycolide are particularly preferable. As lactide any of L-lactide, D-lactide, DL-lactide and racemic lactide can be used.

The cyclic ester compound to be used may contain a hydroxy acid and water, but the amount of them is preferably 30 mol % or less based on the cyclic ester compound. During reaction, predetermined amounts of the hydroxy acid, water and an alcohol may be added to the cyclic ester compound for the purpose of adjusting a reaction rate and the molecular weight of the produced copolymer. Similarly, the amounts of them are preferably 30 mol % or less based on the cyclic ester compound.

If the feed composition ratio of the cyclic ester compound to aspartic acid is too high, aspartic acid is scarcely incorporated into the polymer, so that polyhydroxycarboxylic acids alone such as PLA, PGA, PLGA and polycaprolactone are liable to be produced and hence it is difficult to obtain the copolymer which is the target product of the present invention. On the other hand, if the feed composition ratio of aspartic acid is too high, the block chain of the lactic acid unit and/or the glycolic acid unit scarcely extends unpreferably. In view of the above points, the feed composition ratio of aspartic acid to the cyclic ester compound is preferably in the range of about 1:1 to 1:50.

According to the preparation process of the present invention, the polymer can be sufficiently obtained, even if any solvent is not used during the reaction. However, for the purposes of shortening a reaction time and increasing the molecular weight of the produced polymer, a certain kind of catalyst may be used. Examples of the preferable catalyst include metals such as tin, zinc and titanium, metallic salt compounds such as tin octanoate and tin tetrachloride, organic acids and inorganic acids.

The control of a reaction temperature is important. During the whole reaction steps, the reaction is carried out preferably in the range of 120° C. to 230° C. However, in an early stage of the reaction, the reaction is preferably carried out at a high temperature of at least 140° C. in order to accelerate the dehydration of aspartic acid. This temperature is preferably in the range of 160° C. to 230° C., more preferably 180° C. to 220° C. In the latter half of the reaction, the temperature is preferably lower than in the early stage of the reaction in order to inhibit the decomposition of the produced polymer. This temperature is preferably in the range of 120° C. to 200° C.

A polymerization reaction mechanism in the preparation process of the present invention is different from a polymerization mechanism of a conventional method in which aspartic acid, lactic acid and/or glycolic acid are heated and dehydrated (hereinafter referred to as "the direct dehydrocondensation method"). This can easily be understood from a fact that a reaction proceeding state, the molecular weight of the produced polymer, a molecular weight distribution and a yield in the process of the present invention are different from those in the conventional method.

Next, a suitable embodiment of the present invention will be described in accordance with an example in which the cyclic ester compound is lactide and/or glycolide.

In the early stage of the reaction, glycolide and/or lactide having a melting point in the vicinity of 80 to 90° C. is first molten and stirred, while an unmolten aspartic acid powder floats. Afterward, aspartic acid begins to polymerize by heating, while dehydrated. By the utilization of water generated by the dehydration of aspartic acid, the ring of lactide and/or glycolide is opened, and while a hydroxy acid produced by the ring opening opens the rings of other lactide and/or glycolide, the polymerization proceeds. Afterward, copolymerization occurs between aspartic acid or the polymer of aspartic acid and lactide and/or the polymer of glycolide, whereby aspartic acid or the polymer of aspartic acid which has been in a granular state is solubilized and becomes transparent, and a reaction solution becomes uniformed. Gradually, the viscosity of the reaction solution increases.

On the other hand, when the direct dehydrocondensation method, wherein aspartic acid is reacted with lactic acid and/or glycolic acid, is conducted, aspartic acid is quickly dissolved in lactic acid and/or glycolic acid in the early stage of the reaction by heating, and a transparent and uniform solution is formed. As the result, aspartic acid is copolymerized with lactic acid and/or glycolic acid without polymerization of aspartic acid each other to form a copolymer having high randomness.

According to the preparation process of the present invention, after most of aspartic acid or the polymer of aspartic acid is consumed and the reaction solution becomes uniformed, i.e., in the latter half of the reaction, the pressure of the reaction system is preferably reduced to accelerate the dehydration. For the acceleration of the dehydration, a solvent which can make water azeotropic may be added, and reflux may be then carried out to remove water from the resultant effluent.

A reaction time can be suitably decided in consideration of the reaction temperature, the presence/absence of the catalyst and the molecular weight of the polymer, but it is in the range of about 2 to 100 hours.

After completion of the reaction, the purifying isolation of the produced polymer from the reaction mixture can be performed by a known purifying isolation technique such as a reprecipitation method or a separating precipitation method. For example, the reaction mixture is dissolved in dimethylformamide (DMF), and the solution is then poured into water. Afterward, the insoluble polymer precipitate is collected by filtration or centrifugal separation. The preparation process of the present invention permits the production of the polymer having a higher molecular weight and a narrower molecular weight distribution, as compared with the direct dehydrocondensation method. In addition, the collection ratio of the polymer by a purification such as the reprecipitation is high.

One aspect of the copolymer of the present invention is the polymer obtained by heating the mixture of aspartic acid and lactide and/or glycolide, and this copolymer is different in the structure from a copolymer obtained by the conventional direct dehydrocondensation method. This difference of the structure can be confirmed by a known analytical means. That is to say, for example, in NMR spectra, peaks having low intensities are different, whereby it can be confirmed that the extent of branching and the blocking tendency are definitely different.

Furthermore, the difference of the structure between both the methods leads to a difference of the hydrolysis behavior. For example, reference will be made to the same copolymers in which the composition ratio of the unit derived from aspartic acid to the unit derived from the hydroxy acid is 1:5. In the case of the copolymer of the present invention, the whole polymer becomes water-soluble relatively rapidly (in a time of several hours to several tens of hours) in water at a temperature in the vicinity of a body temperature and at the same pH as in the human body, and it once disappears, but it becomes water insoluble again in a period of several days to several tens of days to produce a precipitate. On the other hand, in the case of the copolymer obtained by the direct dehydrocondensation method, the copolymer partially becomes water-soluble, but the water-insoluble polymer is continuously held over several tens days.

In addition, the difference of the structure between both the methods also appears as a difference of solubility. Moreover, with regard to the molecular weight distribution, a difference can also be observed.

The difference of the structure is, needless to say, based on the difference between the preparation methods. The structure of the copolymer according to the present invention is derived from its specific preparation process.

Furthermore, the present invention covers a copolymer including at least the aspartic acid unit and the lactic acid unit and/or the glycolic acid unit as the repeating structure units which can be obtained by first heating a mixture of aspartic acid and lactide and/or glycolide and then hydrolyzing the succinimide unit of the resultant polymer to open a ring (this copolymer will be hereinafter referred to as "the hydrolysis type copolymer"). One example of this hydrolysis type copolymer is a polymer having the structure represented by the structural formula (13):

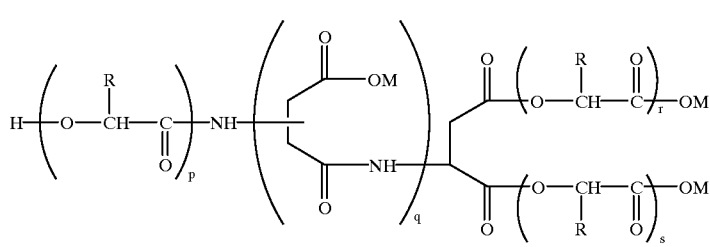

(13)

wherein p, r and s are each 0 or a positive integer, provided that three of p, r and s are not simultaneously 0; q is 0 or a positive integer, and $(p+r+s)/(q+1)=2$ to 100; R is a hydrogen atom or a methyl group; and M is a metal or a hydrogen atom.

A difference between the structural formulae (14) and (15) is the presence/absence of an opened imide ring. A composition ratio between the opened ring structure and the unopened ring structure can be changed by adjusting the extent of the hydrolysis, and the copolymer having any composition ratio is within the scope of the present invention.

The aspartic acid unit contained in the structure of the copolymer according to the present invention is a unit in which an α-amide type monomer unit and β-amide type monomer unit can simultaneously exist, and a ratio between both the amide type monomer units is not particularly limited.

The hydrolysis type copolymer can be prepared by suspending or dissolving the copolymer having the succinimide unit obtained by the above preparation process in water or a mixed solvent of a water-readily soluble solvent and water, and then simply heating the suspension or the solution, or adding an aqueous alkali solution thereto. The water-readily soluble solvent means a solvent which can dissolve at least 5% by weight of water therein, and examples of the water-readily soluble solvent include alcohols such as methanol and ethanol, acetone and acetonitrile. In the case that the alkali is added, the molecular weight of the copolymer lowers if the alkali is excessively added. Hence, this point should be noted.

As the aqueous alkali solution for use in the hydrolysis, a known aqueous solution can be used. Example of the aqueous alkali solution include an aqueous sodium hydroxide solution, an aqueous potassium hydroxide solution, an aqueous ammonia solution and an aqueous sodium carbonate solution.

The hydrolysis scarcely proceeds under acidic conditions. On the other hand, strong alkali conditions are also inconvenient, because the cleavage of the polymer chain easily occurs. In consideration of these points, it is preferred that the hydrolysis is carried out in the pH range of 6 to 11.

In the case that a usually known PLA or PLGA is an oligomer having a low molecular weight of several thousand or so, it is in a syrup state or a sticky solid, whereas the copolymer of the present invention is a less sticky solid at room temperature (ordinary temperature) though it has a low molecular weight, so that it can be easily handled. The glass transition point (Tg) of the copolymer is in the range of 40° C. or more (about 40 to 60° C.), and it is easily molten at a relatively low temperature (e.g., 100° C. or less). In addition, its melting viscosity is lower than the already existing PLA, PLGA or the like, and so it can be conveniently molten and mixed with an sustained releasing drug.

The copolymer of the present invention can be readily dissolved in various kinds of organic solvents and can be easily molten and molded at a relatively low temperature, and hence it can be molded into microspheres, microcapsules or the like. Therefore, the copolymer is useful as a resin for the base material of a sustained releasing drug.

That is to say, the employment of the copolymer according to the present invention enables the preparation of the sustained releasing drug comprising this copolymer and a drug. This sustained releasing drug may take the capsule form in which an outer phase is constituted of the copolymer, and an inner phase is constituted of the drug. Alternatively, the sustained releasing drug may take the sphere form comprising a mixture of the copolymer of the present invention and the drug.

The content of the present invention will be described in detail in accordance with examples. Incidentally, the values of physical properties shown in the examples were measured as follows.

(1) Weight-average Molecular Weight (Mw) and Molecular Weight Distribution (Mw/Mn) of a Polymer A sample was dissolved in dimethylformamide (concentration=0.5% by weight), and the weight-average molecular weight (Mw) and the molecular weight distribution (Mw/Mn) of the polymer were measured by gel permeation chromatography (GPC). As a control substance, poly-styrene was used.

(2) Infrared Absorption (IR) Spectrum

A polymer sample powder was well mixed with a KBr powder, and the mixture was then pressed while deaerated to form tables, and a spectrum was then measured by an FT-IR device (Fourier analysis type, integrating type infrared spectrometer).

(3) Nuclear Magnetic Resonance (NMR) Spectrum

A sample was dissolved in deuterized dimethyl sulfoxide (concentration=7% by weight), and H-NMR spectrum (400 MHz) and C-NMR spectrum (100 MHz) were measured at room temperature by the use of a nuclear magnetic resonance measuring device.

(4) Measurement by a Differential Scanning Calorimeter (DSC)

Measurement was done at −50° C. to 250° C. under a temperature rise velocity of 10° C./min by a differential scanning calorimeter.

(5) Solubility Test of a Polymer 200 mg of a polymer sample were added to 2 ml of a solvent, heated up to 40 to 50° C. with stirring, and then cooled to room temperature again, and a solubility of the polymer was inspected. Evaluation was made in accordance with 4 grades of "completely dissolved", "half dissolved", "swelled" and "undissolved".

EXAMPLE 1

13.3 g (0.1 mol) of L-aspartic acid and 28.8 g (0.2 mol) of L-lactide were placed in a glass reactor equipped with a stirring device and a vent. In this case, a molar ratio of fed aspartic acid to lactic acid became 1:4. The reactor was immersed in an oil bath at 180° C., followed by stirring. Lactide having a melting point of 98° C. was molten, and heating was continued in a condition that a white powder of insoluble aspartic acid was floating. The powder gradually disappeared in a period of about 30 minutes to 1 hour, and the viscosity of the yellow reaction solution rose. After 1.5 hours from the start of the heating, the pressure in the reaction system was slowly reduced, so that 1 mmHg was reached after 2 hours. The heating was further continued for 2 hours, and the reactor was taken out of the oil bath and the reaction solution was collected and then cooled for solidification. The resultant lightly yellowish brown semitransparent solid was ground to obtain a powdery polymer. An Mw and an Mw/Mn of the obtained polymer was 6500 and 7.4, respectively.

After 10 g of this polymer were dissolved in 20 g of DMF, the solution was poured into 400 ml of water, and the resultant precipitate was then collected to thereby purify the polymer. A purification yield was 81%. An Mw and an Mw/Mn of the purified polymer was 9400 and 1.22, respectively.

For the thus purified polymer, IR measurement was carried out, and as a result, a broad absorption was present at 3420 cm$^{-1}$, and other characteristic absorption peaks were observed at 3000 cm$^{-1}$, 2950 cm$^{-1}$, 1723 cm$^{-1}$, 1720 cm$^{-1}$, 1460 cm$^{-1}$, 1390 cm$^{-1}$, 1360 cm$^{-1}$, 1210 cm$^{-1}$, 1190 cm$^{-1}$, 1140 cm$^{-1}$, 1100 cm$^{-1}$ and 1050 cm$^{-1}$.

The H-NMR of the purified polymer was measured, and in consequence, there were observed a peak derived from a methyl proton of a lactic acid unit at 1.3 to 1.6 ppm, a peak derived from a methylene proton of a succinimide unit at 2.5 to 3.3 ppm, a peak derived from a methine proton of the lactic acid unit in the vicinity of 5.0 ppm, and a peak derived from a methine proton of the succinimide unit in the vicinity of 5.2 ppm. In addition, peaks derived from amide protons having the following structural formulae (14) and (15) were confirmed at 8.1 to 8.8 ppm.

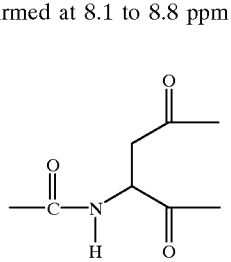

(14)

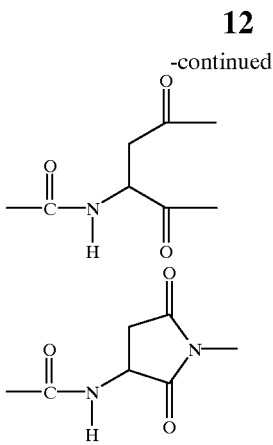

(14)

(15)

Furthermore, peaks derived from methyl protons having the above structural formulae (14) and (15) were confirmed at 4.6 to 4.7 ppm.

Additionally, in the H-NMR spectrum, there were present peaks derived from, for example, polymer terminals and branched portions at 1.0 ppm, 3.7 ppm, 4.0 ppm, 4.2 ppm, 5.4 ppm, 5.6 ppm and 7.2 ppm, though the intensity of these peaks was low.

According to the results of the NMR measurement, a composition ratio of a unit derived from aspartic acid (an aspartic acid unit and a succinimide unit) to the lactic acid unit in the polymer was 1:3.9.

On the basis of the analysis of the NMR spectrum and the IR spectrum, the structure of the obtained polymer could be presumed to be substantially as shown by the following structural formula (16).

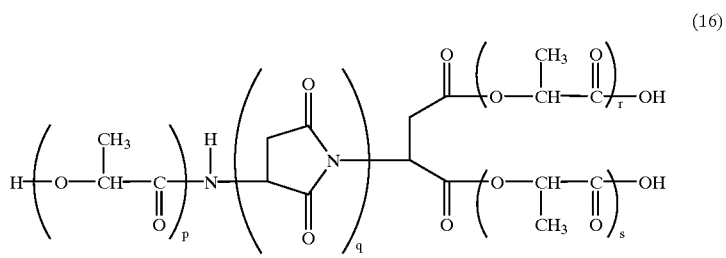

(16)

wherein p, q, r and s are each 0 or a positive integer.

However, it could be presumed that a part of the succinimide unit in the structural formula (16) was opened, and structural moieties of the following structural formulae (17) and (18) were contained therein.

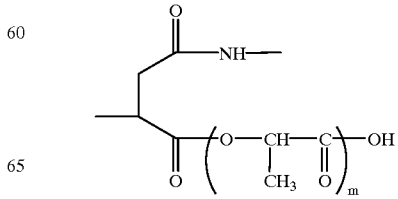

(17)

-continued

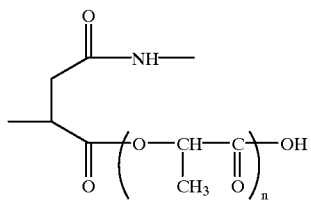

(18)

wherein m and n are each 0 or a positive integer.

Furthermore, the obtained polymer was an unsticky solid at ordinary temperature, and according to DSC measurement, the glass transition point was shown at 41° C. No absorption of heat by melting a crystal was shown so that the polymer was noncrystalline.

The solubilities of the polymer in various solvents were as follows:
Completely dissolved: Dimethyl formamide, dimethyl sulfoxide, acetone, tetrahydrofuran, acetonitrile and ethyl acetate.
Half dissolved (a part of insolubles remained): Chloroform.
Swelled (or gummed): Methanol, ethanol and 2-propanol.
Undissolved: Water and toluene.

The obtained polymer powder was placed in a test tube and a sufficient amount of a phosphoric acid buffer solution having a pH of 7.3 was added thereto, and it was kept in a thermostatic chamber at 37° C. The polymer powder disappeared in a period of several hours to 20 hours, and the solution in the test tube became slightly yellow semitransparent. This reason is that an imide ring in the polymer structure was hydrolyzed to produce a carboxyl group, so that the polymer became water-soluble.

REFERENCE EXAMPLE 1

L-lactide alone was heated at 180° C. in the same manner as in Example 1, so that a slightly yellow semitransparent solution could be formed, but viscosity did not rise. The solution was cooled and hence solidified, and the resultant solid was collected and then inspected. As a result, it was apparent that the solid was L-lactide containing a small amount, i.e., several percent by weight of a lactic acid oligomer (dimer to decamer or so).

REFERENCE EXAMPLE 2

Aspartic acid alone was heated at 180° C. in the same manner as in Example 1, and it scarcely changed in about 4 hours. An aspartic acid powder was collected.

Next, aspartic acid was heated at 220° C. for 2 hours, so that a brown powder was obtained. By NMR and IR measurement, it was confirmed that this brown powder was a polysuccinimide. Its Mw was 15,000.

In DSC measurement, this polysuccinimide did not show a definite melting heat absorption peak, and it only thermally decomposed at 250° C. or more.

The solubilities of the obtained polysuccinimide in various solvents were as follows:
Half dissolved (a part of insolubles remained): Dimethylformamide.
Undissolved: Chloroform, tetrahydrofuran, acetone, acetonitrile, ethanol, methanol, water and toluene.

EXAMPLE 2

13.3 g (0.1 mol) of L-aspartic acid and 36.0 g (0.25 mol) of L-lactide were placed in a glass reactor equipped with a stirring device and a vent. In this case, a molar ratio of fed aspartic acid to lactic acid became 1:5. The reactor was immersed in an oil bath at 180° C., followed by stirring. Lactide having a melting point of 98° C. was molten, and heating was continued in a condition that a white powder of insoluble aspartic acid was floating. The powder gradually disappeared in a period of about 30 minutes to 1 hour, and the viscosity of the yellow reaction solution rose. After 1.5 hours from the start of the heating, the pressure in the reaction system was slowly reduced, so that 1 mmHg was reached after 2 hours. After the heating was further continued for 2 hours, the temperature of the oil bath was lowered to 160° C., and the reaction was further continued for 15 hours. The reactor was taken out of the oil bath, and the reaction solution was collected and then cooled for solidification. The resultant lightly yellowish brown semitransparent solid was ground to obtain a powdery polymer. An Mw and an Mw/Mn of the polymer was 14,700 and 1.38, respectively.

After 10 g of this polymer were dissolved in 20 g of DMF, the solution was poured into 400 ml of water, and the resultant precipitate was then collected to thereby purify the polymer. A purification yield was 94%. An Mw and an Mw/Mn of the purified polymer was 16,300 and 1.37, respectively.

According to the results of the NMR measurement, a composition ratio of a unit derived from aspartic acid (an aspartic acid unit and a succinimide unit) to the lactic acid unit in the polymer was 1:5.1.

According to DSC measurement, the glass transition point was shown at 52° C. No absorption of heat by melting a crystal was shown so that the polymer was noncrystalline.

The solubilities of the polymer in various solvents were as follows:
Completely dissolved: Dimethyl formamide, dimethyl sulfoxide, acetone, tetrahydrofuran, acetonitrile and ethyl acetate.
Half dissolved (a part of insolubles remained): Chloroform.
Swelled (or gummed): Methanol and ethanol.
Undissolved: Water and toluene.

The obtained polymer powder was placed in a test tube, and a sufficient amount of a phosphoric acid buffer solution having a pH of 7.3 was added, and it was kept in in a thermostatic chamber at 37° C. The polymer powder disappeared in a period of several hours to 20 hours, and the solution in the test tube became slightly yellow semitransparent. As in Example 1, an imide ring in the polymer structure was hydrolyzed to produce a carboxyl group, so that the polymer became water-soluble. While the test tube was further allowed to stand in the thermostatic chamber as it was, observation was continued. In consequence, after the lapse of about 12 days, the solution began to whiten, and after the lapse of about 15 days, a white precipitate was observed. This reason is that the water-soluble aspartic acid unit was cleaved by decomposition, and the ratio of the lactic acid unit in the polymer increased, so that it became water-insoluble again. After the lapse of about 19 days, the solution was centrifugally separated to collect a white precipitate, thereby obtaining a white powder in a ratio of 25% by weight of the polymer subjected to the test. The molecular weight of the polymer was measured by GPC, so that an Mw and an Mw/Mn of the polymer were 12,300 and 1.34, respectively.

EXAMPLE 3

106.5 g (0.8 mol) of L-aspartic acid and 288.2 g (2.0 mol) of L-lactide were placed in a glass reactor equipped with a stirring device and a vent. In this case, a molar ratio of fed aspartic acid to lactic acid became 1:5. The reactor was immersed in an oil bath at 180° C., followed by stirring. Lactide having a melting point of 98° C. was molten, and heating was continued in a condition that a white powder of insoluble aspartic acid was floating. The powder gradually disappeared in a period of about 30 minutes to 1 hour, and the viscosity of the yellow reaction solution rose. After 2.5 hours from the start of the heating, the pressure in the reaction system was slowly reduced, so that 1 mmHg was reached after 3 hours. After the heating was further continued for 11 hours, the reactor was taken out of the oil bath, and the reaction solution was collected and then cooled for solidification. The resultant lightly yellowish brown semitransparent solid was ground to obtain a powdery polymer. An Mw and an Mw/Mn of the polymer was 26,000 and 1.32, respectively.

According to the results of NMR measurement, a composition ratio of a unit derived from aspartic acid to the lactic acid unit in the polymer was 1:5.0.

According to DSC measurement, the glass transition point was shown at 52° C. No absorption of heat by melting a crystal was shown so that the polymer was noncrystalline.

EXAMPLE 4

6.7 g (0.05 mol) of L-aspartic acid and 36.0 g (0.25 mol) of L-lactide were placed in a glass reactor equipped with a stirring device and a vent. In this case, a molar ratio of fed aspartic acid to lactic acid became 1:10. The reactor was immersed in an oil bath at 180° C., followed by stirring. Lactide having a melting point of 98° C. was molten, and heating was continued in a condition that a white powder of insoluble aspartic acid was floating. The powder gradually disappeared in a period of about 1 hour, and the viscosity of the yellow reaction solution rose. After 2.5 hours from the start of the heating, the pressure in the reaction system was slowly reduced, so that 1 mmHg was reached after 3 hours. The temperature of the oil bath was lowered to 160° C., and the reaction was further continued for 6 hours. At this point, the reaction solution was sampled, and a molecular weight was then measured. As a result, an Mw of the sample was 8,800. After the reaction was further continued for 9 hours, the reactor was taken out of the oil bath, and the reaction solution was collected and then cooled for solidification. The resultant lightly yellowish brown semitransparent solid was ground to obtain a powdery polymer. An Mw and an Mw/Mn of the polymer was 17,000 and 1.39, respectively.

After 10 g of this polymer were dissolved in 20 g of DMF, the solution was poured into 400 ml of water, and the resultant precipitate was then collected to thereby purify the polymer. A purification yield was 96%. An Mw and an Mw/Mn of the purified polymer was 17,800 and 1.35, respectively.

According to the results of NMR measurement, a composition ratio of a unit derived from aspartic acid to the lactic acid unit in the polymer was 1:10.4.

According to DSC measurement, the absorption of heat was shown at 49° C.

The solubilities of the polymer in various solvents were as follows:
Completely dissolved: Dimethyl formamide, dimethyl sulfoxide, acetone, tetrahydrofuran, acetonitrile, ethyl acetate, chloroform and hot toluene.
Swelled (or gummed): Methanol and ethanol.
Undissolved: Water.

EXAMPLE 5

13.3 g (0.1 mol) of L-aspartic acid and 144.1 g (1.0 mol) of L-lactide were placed in a glass reactor equipped with a stirring device and a vent. In this case, a molar ratio of fed aspartic acid to lactic acid became 1:20. The reactor was immersed in an oil bath at 180° C., followed by stirring. Lactide having a melting point of 98° C. was molten, and heating was continued in a condition that a white powder of insoluble aspartic acid was floating. The powder gradually disappeared in a period of about 30 minutes to 1 hour, and the viscosity of the yellow reaction solution rose. After 2.5 hours from the start of the heating, the pressure in the reaction system was slowly reduced, so that 1 mmHg was reached after 3 hours. After the heating was further continued for 12 hours, the reactor was taken out of the oil bath, and the reaction solution was collected and then cooled for solidification. The resultant lightly yellowish brown semitransparent solid was ground to obtain a powdery polymer. An Mw and an Mw/Mn of the polymer was 21,000 and 1.26, respectively.

After 10 g of this polymer were dissolved in 20 g of DMF, the solution was poured into 400 ml of water, and the resultant precipitate was then collected to thereby purify the polymer. A purification yield was 95%. An Mw and an Mw/Mn of the purified polymer was 21,000 and 1.25, respectively.

According to the results of the NMR measurement, a composition ratio of a unit derived from aspartic acid (an aspartic acid unit and a succinimide unit) to the lactic acid unit in the polymer was 1:19.5.

According to DSC measurement, the glass transition point was shown at 50° C. No absorption of heat by melting a crystal was shown so that the polymer was noncrystalline.

The solubilities of the polymer in various solvents were as follows:
Completely dissolved: Dimethyl formamide, dimethyl sulfoxide, acetone, tetrahydrofuran, acetonitrile, ethyl acetate and hot toluene.
Swelled (or gummed): Methanol and ethanol.
Undissolved: Water.

The obtained polymer powder was placed in five test tubes, and a sufficient amount of a phosphoric acid buffer solution having a pH of 7.3 was added, followed by hydrolysis was conducted in a thermostatic chamber at 37° C. The test tube was picked up one by one after passed one day, 5 days, 9 days, 19 days and 31 days, and insoluble polymer powder was collected from the test tube by centrifugally separation, and then they were dried. The weight of polymers collected, after passed one day, 5 days, 9 days, 19 days and 31 days, were 63%, 61%, 70%, 75% and 45% respectively, and Mw were 24000, 26000, 34000, 17000 and 9000 respectively.

COMPARATIVE EXAMPLE 1

Into a glass reactor equipped with a stirring device and a vent, 200 g of 90% aqueous solution of L-aspartic acid was placed, and the reactor was immersed in an oil bath at 180° C., followed by stirring. When distilling water was almost finished, the pressure in the reaction system was slowly reduced (20 mmHg). After the heating was further continued for 5 hours, the reactant was sampled in a little amount. The sample was a millet jelly-like oligomer having Mw of 9500 and glass transition point of 18° C. Furthermore, under the reduced pressure (20 mmHg), the reaction was continued at 160° C. After 20 hours passed, the reactor was taken out of the oil bath, and the reaction solution was collected and then cooled for solidification. The polymer obtained was polylactic acid having Mw of 17000, glass transition point of 39° C. and melting point of 136° C.

The solubilities of the polymer in various solvents were as follows:

Completely dissolved: Dimethyl formamide, dimethyl sulfoxide and chloroform

Undissolved: Acetone, toluene, tetrahydrofuran, acetonitrile, ethyl acetate, ethanol, methanol, 2-propanol and water.

The obtained polymer powder was placed in five test tubes, and a sufficient amount of a phosphoric acid buffer solution having a pH of 7.3 was added, followed by hydrolysis was conducted in a thermostatic chamber at 37° C. The test tube was picked up one by one after passed one day, 5 days, 9 days, 19 days and 31 days, and insoluble polymer powder was collected from the test tube by centrifugally separation, and then they were dried. The weight of polymers collected, after passed one day, 5 days, 9 days, 19 days and 31 days, were 97%, 96%, 92%, 92% and 90% respectively, and Mw were 17000, 17200, 16800, 17000 and 16500 respectively.

EXAMPLE 6

4.21 g of the polymer powder obtained in Example 1 was suspended in 150 ml of distilled water. The pH of the resultant suspension was 4. While the solution was stirred and the pH of the solution was watched, a 1N aqueous sodium hydroxide solution was slowly added dropwise thereto. Each time the aqueous sodium hydroxide solution was added dropwise, the pH of the solution rose from 4 to 9, and immediately it lowered to 4. As the amount of the dropped aqueous sodium hydroxide solution increased, the return of the pH tended to be slow. The polymer particles suspended in the solution were gradually solubilized, and when the amount of the dropped aqueous sodium hydroxide solution reached 0.4 g, most of the polymer particles disappeared and the solution became slightly yellow semitransparent. The pH of the solution was 6.2. This solution was concentrated to dryness, and the resultant yellowish brown solid was dissolved in methanol. Afterward, the solution was poured into acetonitrile to bring about reprecipitation, and the thus reprecipitated white polymer solid was then collected. An Mw and an Mw/Mn of the obtained polymer were 9,000 and 1.2, respectively.

In the IR spectrum of this polymer, there were observed the absorption peaks shown in the IR spectrum of the polymer in Example 1 as well as an intensive absorption peak characterized by an amide structure at 1620 cm$^{-1}$.

EXAMPLE 7

0.5 g of the polymer powder obtained in Example 3 was dissolved in 5 ml of acetonitrile, and the solution was poured into 50 ml of cotton seed oil containing 0.1% of lecithin. Then, it was stirred by a homogenizer at 15000 rpm for 3 minutes to prepare a oil-in-oil emulsion. the pressure in the vessel containing the emulsion was slowly reduced, and it was stirred for 2 hours at 40° C. to remove acetonitrile. The oil was given back at room temperature and atmospheric pressure. Into the oil, 25 ml of hexane was added, and the deposited polymer particle was collected by filtration. Furthermore, the particle was washed well and dried. By microscope observation, it was confirmed that the polymer powder was microsphere having diameter of about several μm to several tens of μm.

EXAMPLE 7

1.5 g of the copolymer obtained in Example 5 was dissolved in 10 ml of chloroform. A solution, in which 100 mg of acetaminophen was dissolved in 1 ml of water, was poured into the chloroform solution, and then, it was stirred by a homogenizer at 12000 rpm for 3 minutes to prepare an emulsion. The emulsion was slowly added dropwise by a pipette into 200 ml of 1% aqueous solution of polyvinylalcohol (polymerization degree: about 500). The pressure in the vessel containing the emulsion obtained was reduced to remove chloroform. The deposited polymer particle was collected by filtration. Furthermore, the particle was washed by water and dried to obtain a microsphere containing a desired pharmaceutical component.

As described above, according to the present invention, there can be provided a novel copolymer having a succinimide unit and/or an aspartic acid unit as well as a lactic acid unit and/or a glycolic acid unit as repeating structural units, and a process for preparing the copolymer. This copolymer is solid at ordinary temperature, has a relatively low melting point, shows a specific hydrolysis behavior, and is useful as a novel biologically absorbable polymer, for example, as a base material for a sustained releasing drug.

In addition, according to the preparation process of the present invention, a novel copolymer having a high molecular weight and a narrow molecular weight distribution can be obtained in a high yield.

What is claimed is:

1. A copolymer having a weight-average molecular weight of 1,000 to 100,000 which comprises, as repeating structure units, both of a succinimide unit represented by the structural formula (1)

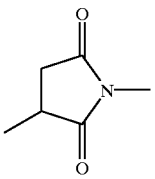

(1)

and a hydroxycarboxylic acid unit represented by the structural formula (2)

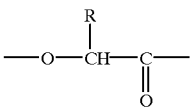

(2)

wherein R is a methyl group or a hydrogen atom.

2. The copolymer according to claim 1 wherein the ratio of the succinimide unit represented by the structural formula (1) is in the range of 1 to 33 mol %, and the ratio of the hydroxycarboxylic acid unit represented by the structural formula (2) is in the range of 67 to 99 mol %.

3. The copolymer according to claim 1 which comprises both of a polysuccinimide segment represented by the structural formula (3)

(3)

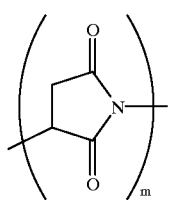

wherein m is an integer of 1 to 100,
and a polyhydroxycarboxylic acid segment represented by the structural formula (4)

(4)

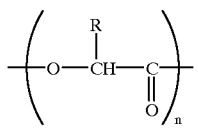

wherein R is a methyl group or a hydrogen atom; and n is an integer of 1 to 1,000,
and in which the ratio of the succinimide unit is in the range of 1 to 33 mol %, and the ratio of the hydroxycarboxylic acid unit is in the range of 67 to 99 mol %.

4. The copolymer according to claim 1 which is a branched copolymer having all of a segment A represented by the structural formula (5)

(5)

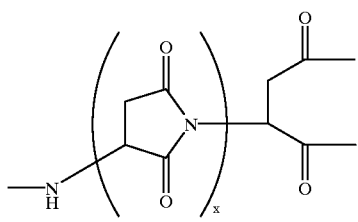

wherein x is an integer of 1 to 100,
a segment B represented by the structural formula (6)

(6)

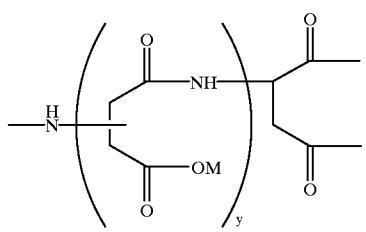

wherein y is 0 or a positive integer of 100 or less; and M is a metal or a hydrogen atom,
and a segment C represented by the structural formula (7)

(7)

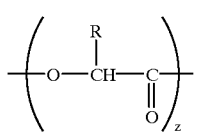

wherein z is an integer of 4 to 1,000; and R is a methyl group or a hydrogen atom,
and in which the ratio of a unit containing a structure represented by the following structural formula (8) derived from aspartic acid is in the range of 1 to 33 mol %, (8)

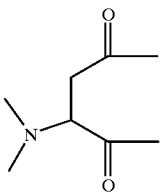

and the ratio of the hydroxycarboxylic acid unit is in the range of 67 to 99 mol %, and a molecular terminal comprises at least one group selected from the group consisting of an amino group, a hydroxy group, a carboxyl group and a carboxylate group.

5. The copolymer according to claim 1 which contains a repeating structure unit represented by the structural formula (9)

(9)

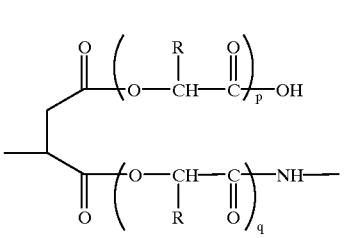

wherein p and q is each 0 or a positive integer of 1,000 or less; and R is a methyl group or a hydrogen atom, and/or a repeating structure unit represented by the structural formula (10)

(10)

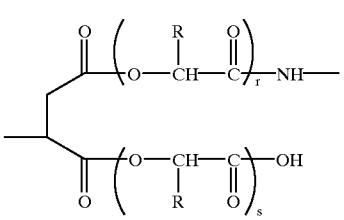

wherein r and s is each 0 or a positive integer of 1,000 or less; and R is a methyl group or a hydrogen atom, and in which the ratio of a unit containing a structure represented by the following structural formula (11) derived from aspartic acid in the copolymer is in the range of 1 to 33 mol %, (11)

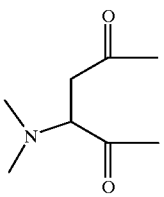

and the ratio of the hydroxycarboxylic acid unit is in the range of 67 to 99 mol %.

6. The copolymer according to claim 1 which is represented by the following structural formula (12)

(12)

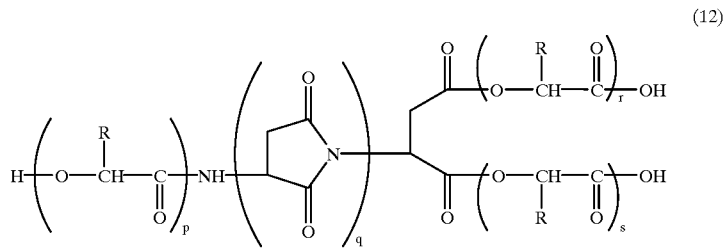

wherein p, r and s are each 0 or a positive integer, provided that three of p, r and s are not simultaneously 0; q is an integer of 1 or more, and (p+r+s)/(q+1) is in the range of 2 to 100; and R is a hydrogen atom or a methyl group.

7. A copolymer represented by the following structural formula (13), which is obtained from the copolymer of claim 1, (13)

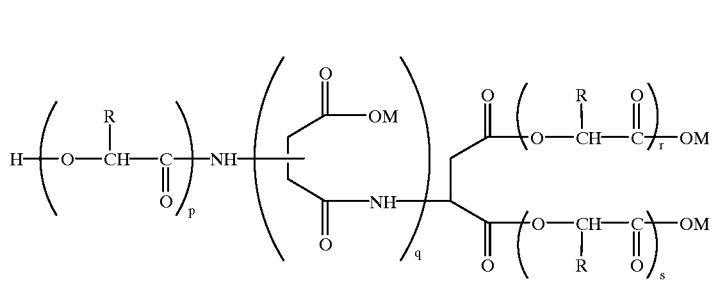

wherein p, r and s are each 0 or a positive integer, provided that three of p, r and s are not simultaneously 0; q is an integer of 0 or a positive integer, (p+r+s)/(q+1) is in the range of 2 to 100; and R is a hydrogen atom or a methyl group; and M is a metal or a hydrogen atom.

8. The copolymer according to claim 1 which has a Tg of 40° C. or more, and is molten at 100° C. or less.

9. A process for preparing a copolymer according to claim 1, which comprises a polymerization step of heating a mixture of aspartic acid and a cyclic ester compound to obtain the copolymer.

10. The process for preparing the copolymer according to claim 9 which further contains a hydrolysis step of hydrolyzing the succinimide unit of the copolymer obtained in the polymerization step to open at least a part of the rings of the copolymer, thereby obtaining the copolymer having both of at least the aspartic acid unit and the hydroxycarboxylic acid unit.

11. The process for preparing the copolymer according to claim 9 wherein a mixed molar ratio of aspartic acid to the cyclic ester compound is in the range of 1/1 to 1/50.

12. The process for preparing the copolymer according to claim 9 wherein the cyclic ester compound is lactide and/or glycolide.

13. The process for preparing the copolymer according to claim 9 wherein a mixture of aspartic acid and lactide and/or glycolide is heated at 120 to 230° in the polymerization step.

14. The process for preparing the copolymer according to claim 10 wherein the hydrolysis is carried out at a pH of 6 to 11 in the hydrolysis step.

* * * * *